United States Patent [19]

Graham et al.

[11] 4,091,094

[45] May 23, 1978

[54] 9-AZARIBOFLAVIN AND PHARMACEUTICAL COMPOSITION CONTAINING SAME

[75] Inventors: Donald W. Graham, Mountainside; Edward F. Rogers, Middletown, both of N.J.

[73] Assignee: Merck & Co., Inc., Rahway, N.J.

[21] Appl. No.: 716,497

[22] Filed: Aug. 23, 1976

[51] Int. Cl.$^2$ .................... A61K 31/525; C07H 19/22
[52] U.S. Cl. ...................... 424/180; 536/18; 536/19; 536/22; 424/251; 544/251
[58] Field of Search ............ 536/19; 424/180

[56] References Cited

U.S. PATENT DOCUMENTS 2,261,608   11/1941   Tishler et al. .................. 536/19

OTHER PUBLICATIONS

Dornow et al. "Chem. Ber.", vol. 93, pp. 1093–1102, 1960.
Israel et al. "Jour. Heterocycl. Chem.," vol. 10, pp. 209–212, 1973.
Israel et al. "Jour. Med. Chem.", vol. 16, No. 5, pp. 520–524, 1973.

*Primary Examiner*—Johnnie R. Brown
*Attorney, Agent, or Firm*—Walter Patton

[57] ABSTRACT

The novel compound 9-azariboflavin is prepared. This compound has anticoccidial, antiprotozoal and antiparasitic activity. It is particularly useful for controlling cecal and/or intestinal coccidiosis when administered in minor quantities to animals, in particular to poultry, usually in admixture with animal sustenance.

6 Claims, No Drawings

9-AZARIBOFLAVIN AND PHARMACEUTICAL COMPOSITION CONTAINING SAME

BACKGROUND OF THE INVENTION

This invention relates to a new chemical compound and the method for preparing the same. It relates further to the use of the new compound for treating and preventing coccidiosis. The compound of the present invention is also effective against protozoal infections especially against human and animal trypanosomiasis and against parasitic infections especially against malaria. This invention still more particularly relates to the novel compound 9-azariboflavin and the use of the same in the control and treatment of coccidiosis.

Coccidiosis is a widespread poultry disease which is produced by infections of protozoa of the genus Eimeria which causes severe pathology in the intestines and ceca of poultry. Some of the most significant of these species are E. tenella, E. acervulina, E. necatrix, E. brunetti and E. maxima. This disease is generally spread by the birds picking up the infectious organism in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

Trypanosomiasis is a term used to describe a group of allied protozoal diseases, each of which is due to infection with a species of the genus Trypanosoma. They reach their greatest importance in Africa where their presence in enzootic form precludes the keeping of domestic animals throughout the largest part of the continent between 15° N and 20° S latitude. The pathogenic trypanosomes of Africa are considered to be primarily associated with the tsetse flies (glossina) which feed on vertebrate blood. Wherever tsetse are present, trypanosomiasis will also be found in some part of the mammalian population. The clinical findings are typically those of a wasting disease with intermittent fever. Anemia, edema, and cachexia are parts of the syndrome.

The important trypanosomes pathogenic to domestic animals are *T. congolense, T. simiae, T. vivax,* and *T. brucei.* The latter trypanosome is morphologically identical to *T. gambiense,* responsible for human "sleeping sickness" of Africa. A trypanosome found in the Western Hemisphere is *T. cruzi,* which affects both domestic animals and man.

Malaria is a serious parasitic infection normally transmitted by the bite of an infected anopheles mosquito, although it may also be produced by transfusion of blood from an infected donor. It is found most frequently in the tropics and in tropical areas is hyperendemic. In man it is caused most frequently by the parasites *Plasmodium falciparum, P. vivax* and *P. malariae.* The acute phase of the disease is characterized by shaking chills, high fever, sweats and headache. With malaria due to *P. vivax* and *P. malariae* the patient frequently suffers relapse because of the ability of these parasites to harbor in liver cells for extended periods of time. In view of the recurrent nature of the disease, chemotherapy is used not only to treat the acute phases, but also on an extended basis as a prophylactic or suppressive therapy. Although there are now available synthetic chemicals for the treatment of malaria, the search has continued for new and/or improved antimalarials and for compounds effective against strains of Plasmodia resistant to currently available agents.

SUMMARY OF THE INVENTION

This invention is based on the discovery that the novel compound 9-azariboflavin has a surprisingly and unexpectedly high degree of activity against coccidiosis of poultry. Administering a small amount of this compound, preferably in combination with poultry feed, is effective in preventing or greatly reducing the incidence of coccidiosis. The compound is effective against both the cecal form (caused by *E. tenella*) and the intestinal forms (principally caused by *E. acervulina, E. brunetti, E. maxima* and *E. necatrix*).

The novel compound, 9-azariboflavin, of this invention is prepared from the starting materials, 2,3-dimethyl-6-chloro-5-nitropyridine (I) and ribitylamine (II). These starting materials are disclosed in A. Darnow and E.-H. Rohe, Chem. Ber., 93, 1093 (1960) and F. W. Holly et al., J. Am. Chem. Soc., 74, 4047 (1952) which are herein incorporated by reference. The novel compound of the present invention is prepared by treating 2,3-dimethyl-6-chloro-5 -nitropyridine (I) with a slight excess of ribitylamine (II) preferably in the presence of an organic base. The resulting solution is heated under reflux under a nitrogen atmosphere until the reaction is complete and evaporated ty dryness under reduced pressure. The residue is subjected to chromatography on silica gel to obtain pure 2,3-dimethyl-5-nitro-6-(D-ribitylamino)pyridine, (III). The 5-nitro group of the pyridine compound, (III), is reduced with a suitable reagent, such as hydrogen and platinum oxide catalyst, which does not reduce the other unsaturated bonds in the molecule to give the corresponding 5-amino pyridine compound: 2,3-dimethyl-5-amino-6-(D-ribitylamino)pyridine, (IV). The compound, (IV), is reacted with alloxan, (VII), in acetic acid with boric acid catalyst to give the novel compound of and present invention, 9-azariboflavin, (VI).

A preferred process for obtaining (VI) is to react a solution of crude compound (IV) in a suitable organic base, such as pyridine, with 5,5-dichlorobarbituric acid, (V), obtained by the process described in E. Zeigler et al., Monatsh. Chem., 93, 1376 (1962), to give the novel compound of the present invention, 9-azariboflavin, (VI), in pure form. Compound (VI) has the chemical name 7,8-dimethyl-10-(1'-D-ribityl)-3H,10H-2,4-dioxopyrido[3,2-g]pteridine. The process for preparing the novel compound of this invention is set forth in Table I below:

TABLE 1

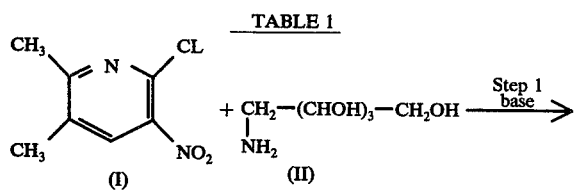

-continued
TABLE 1

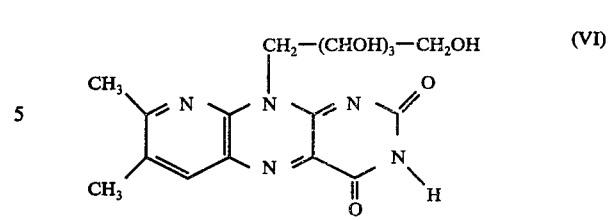
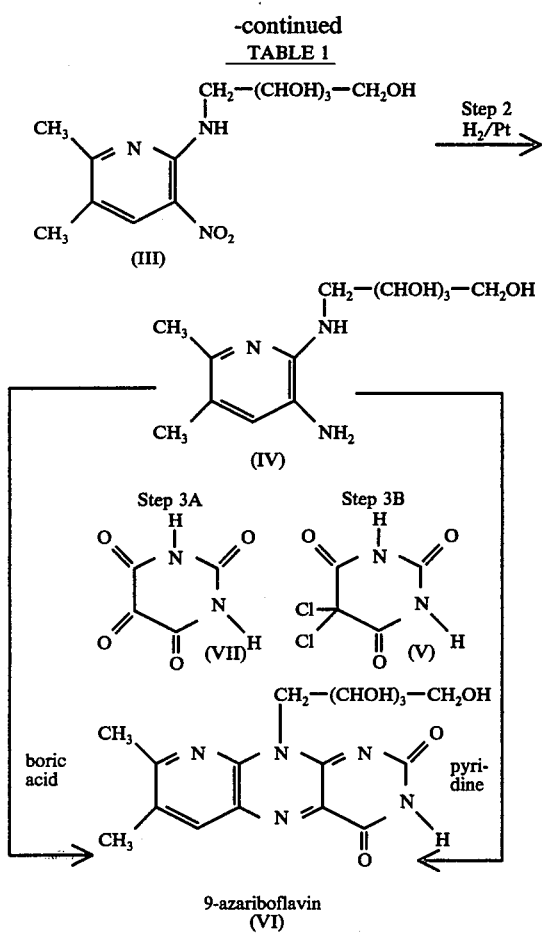

designated 9-azariboflavin.

It is, therefore, a primary object of this invention to provide the novel compound, 9-azariboflavin, which is useful in the control of coccidiosis and protozoal and parasitic infections.

Another object of this invention is to provide a novel anticoccidial agent. Still another object of this invention is to provide novel feed compositions useful for the prevention and suppression of coccidiosis in poultry.

A further object of this invention is to provide a new and useful method for the control of coccidiosis in poultry which comprises administering to the poultry minor amounts of the anticoccidial substance of this invention.

A still further object of this invention is to provide a method for preparing the novel compound 9-azariboflavin.

These and further objects of this invention will become apparent or be described as the description thereof herein proceeds.

DESCRIPTION OF THE PREFERRED EMBODIMENTS

In accordance with this invention, coccidiosis in poultry is controlled or suppressed by administering to the poultry a non-toxic, anticoccidially effective quantity of the compound of the structural formula:

In preparing the novel coccidiostat of this invention, a mixture of the starting materials 2,3-dimethyl-6-chloro-5-nitropyridine, (I), and ribitylamine, (II), are dissolved in an aqueous solution of a mixture of lower alcohols containing 1 to 6 carbon atoms. A suitable mixture is aqueous ethanol and n-butanol. To this is added a trialkyl substituted amine base. A preferred base is diisopropylethylamine. The reaction is carried out in an inert atmosphere with stirring. The reaction time and temperature conditions are not unduly critical. The time of the reaction, however, decreases as the reaction temperature increases. The reaction is most conveniently conducted between the temperature in the range of from about 0° to about 150° C. However, the preferred temperature is the reflux temperature of the solution.

The relative proportions of the components of the reaction mixture of the first step may vary over a relatively wide range. The reactants may be used in stoichiometric amounts, i.e., equal moles of the two reactants may be used, or a slight excess of the amine, II, may be used. The amount of the solvent used may also vary over a wide range. The solvent is used in a quantity sufficient to permit the reaction to proceed at a reasonable rate and facilitate isolation of the reaction product.

At the conclusion of the reaction, the reaction solution is evaporated to dryness under reduced pressure. The residue is chromatographed on silica gel using methanol: chloroform solutions as an eluant. The fractions containing the product are identified by the presence of a prominant orange spot observed by thin layer chromatography. The fractions containing product are evaporated to dryness and the residue triturated with acetone. The resulting crystalline product, (III), is collected by filtration.

In Step 2 the 5-nitro pyridine compound, (III), is reduced to the corresponding 5-amino pyridine compound, (IV), by hydrogenation of an alcoholic solution of compound (III) in a high pressure hydrogenating apparatus using platinum oxide, $PtO_2$, as a catalyst. It is to be understood that upon contact with hydrogen, $PtO_2$ is converted to elemental Pt which is in fact the catalyst. Accordingly, any source which provides Pt is suitable as a catalyst in this reaction. The reaction time and temperature are not unduly critical. The reaction is most conveniently carried out at room temperature. The reaction is stopped when the theoretical amount of hydrogen has been absorbed. The reaction mixture is filtered to remove the catalyst. The filtrate is concentrated and the residue containing the compound (IV) is used without any further purification, in Step 3A or 3B, both of which provide the desired product, 9-azariboflavin, (VI).

In Step 3A, compound (IV) is reacted by warming an acetic acid solution of compound (IV) with alloxan, (VII), in the presence of boric acid catalyst to obtain 9-azariboflavin, (VI).

The preferred process for obtaining compound (VI) is illustrated by Step 3B wherein compound (IV) is treated with an excess of 5,5-dichlorobarbituric acid is a suitable organic base such as pyridine. The organic base is present in large excess and also serves as the solvent.

The reaction is carried out in an inert atmosphere with stirring. The time of the reaction decreases as the reaction temperature increases. The reaction is most conveniently conducted between the temperature in the range of from about 0° to about 150° C. However, the preferred temperature is about 55° C. for about 2 hours.

The relative proportions of the components of the reaction mixture of Step 3B may vary over a relatively wide range. The reactants may be used in stoichiometric amounts, i.e., equal moles of the two reactants may be used, or an excess of alloxan, (VII), may be used. The preferred relative molar proportions of the components is (VII)/(IV), 1.5:1 to 2:1. The most preferred ratio of (VII)/(IV) is about 1.8:1.

The reaction mixture is cooled and insoluble materials removed by filtration. The filtrate, containing the product, is evaporated and the crude product contained in the residue purified by recrystallization from a suitable solvent, such as water.

The novel compound of this invention is orally administered to poultry for the control and prevention of coccidiosis. Any number of conventional methods are suitable for administering the coccidiostat of this invention to poultry, as for example, it may be given in the poultry feed or included in drinking water. The actual quantity of the coccidiostat administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not result in any undesirable effects.

A feed will typically contain from about 0.0025 to about 0.25%, preferably from about 0.0125 to about 0.05% by weight of the coccidiostat of this invention. The optimum levels will naturally vary with the species of Eimeria involved, and can be readily determined by one skilled in the art. Levels of 9-azariboflavin, the coccidiostat of this invention, in poultry feed of from about 0.0225 to about 0.04% by weight of the diet are especially useful.

The quantity or concentration of the novel coccidiostat of this invention in any admixture in which it is administered to the poultry will, of course, vary in accordance with the type of admixture utilized.

Of the various methods of administering the coccidiostat of this invention to poultry, they are most conveniently administered as a component of a feed composition. The novel coccidiostat may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

Suitable compositions also include feed premixes in which the active ingredient is present in relatively large amounts and which are suitable for addition into the feed either directly or after an intermediate dilution or blending step. Such compositions may also be added to the animals feed in the form of a top dressing. Typical carriers or diluents suitable for such compositions include for example, distillers dried grains such as corn distiller's dried grains and corn distiller's grains, corn meal and corn meal germ, citrus meal, fermentation residues, ground oyster shells, wheat shorts and wheat standard middlings, molasses solubles, corncob meal, edible bean mill feed, soyagrits, crushed limestone and the like. The active compound is intimately dispersed throughout the carrier by methods such as grinding, stirring, milling or tumbling. Compositions containing from about 0.1 to 50% by weight, especially from about 0.5 to 25% by weight of the compound 9-azariboflavin are particularly suitable as feed premixes.

Examples of typical feed premixes containing 9-azariboflavin dispersed in a solid inert carrier are:

|   |   | lbs. |
|---|---|---|
| A. | 9-azariboflavin | 6.0 |
|   | Wheat standard middlings | 94.0 |
| B. | 9-azariboflavin | 10.0 |
|   | Corn distiller's dried grains | 90.0 |
| C. | 9-azariboflavin | 20.0 |
|   | Corn germ meal | 30.0 |
|   | Corn distiller's grains | 50.0 |

The compound of this invention has value in the control of trypanosomiasis in domesticated animals, particularly cattle. For this purpose, it may be administered orally with an ingestible carrier as a component of the animal feedstuff, in the drinking water, in salt blocks and in unit dosage forms such as boluses and drenches. The amount of active ingredient required for optimum control of trypanosomiasis varies in accordance with such factors as the species of animal to be treated, the species of infecting parasite, the severity of infection, and whether the compound is employed therapeutically or prophylactically. In general, the compound, 9-azariboflavin, when administered orally to domestic animals in daily doses of from about 1.0 mg. to about 500 mg. per kilogram of animal body weight is highly effective in controlling trypanosomiasis without intolerable toxic effect. When these compounds are to be employed as therapeutic agents, good results are obtained when the animals are fed a daily dose of from about 5 mg. to about 500 mg. and preferably 15 mg. to 250 mg. per kilogram of body weight.

In employing 9-azariboflavin as an antimalarial, the compound is preferably administered orally. Oral dosage forms such as capsules, tablets or powders in which the drug is intimately admixed with a non-toxic solid pharmaceutically acceptable carrier or diluent vehicle are preferred. However, liquid formulations such as syrups, suspensions or elixirs may be used if desired. The compound may also be administered parenterally or intravenously in which case they may be formulated as a solution or suspension in sterile physiologic saline.

The preferred dose level for controlling malaria in humans of 9-azariboflavin is from about 10–2000 mg. per day. As will be understood and appreciated by those skilled in this art, the preferred or optimal dose will depend to some extent upon the species of malaria being treated, the type of treatment being used, i.e., prophylactic or therapeutic. Selection of optimum dose is made without difficulty by a clinician skilled in this art. For example, treatment of acute attacks requires higher and more frequent doses whereas in suppressive or prophylatic therapy lower doses are used but over a longer period of time. When 9-azariboflavin is used against falciparum malaria, oral doses of about 100–1000 mg./day for 1–10 days give good results in treating an acute attack; for preventive therapy the regimen is continued for up to two weeks after the acute stage. Similar treatment is useful against acute attacks of vivax and malariae malaria, but with these strains prophylactic or suppressive therapy is continued for a much longer period of time.

The following non-limiting examples will serve to further illustrate the instant invention.

EXAMPLE 1

2,3-Dimethyl-5-nitro-6-(D-ribitylamino)pyridine (III).

A mixture of 19.2 g. (0.103 moles) of 2,3-dimethyl-6-chloro-5-nitro pyridine (I), 16.4 g. (0.109 moles) of ribitylamine (II), 176 ml. of ethanol, 105 ml. of n-butanol, 67 ml. of water and 105 ml. of diisopropylethylamine was heated under reflux in a nitrogen atmosphere with magnetic stirring for 9 hours. The dark solution was filtered and evaporated under reduced pressure. The dark syrupy residue was chromatographed on 1200 g. of silica gel. Elution with 15% methanol in chloroform gave fractions containing pure product. These were combined and evaporated under reduced pressure. The residue was triturated with acetone and the crystalline product was filtered, washed with cold ethanol and ether, and dried to give 11.2 g. of the product (III), m.p. 141°–142.5° C.

EXAMPLE 2

2,3-Dimethyl-5-amino-6-(D-ribitylamino)pyridine (IV)

A Parr apparatus was charged with 5.5 g. (18.3 mmoles) 2,3-dimethyl-5-nitro-6-(D-ribitylamino)pyridine (III) in 100 ml. of methanol and 200 mg. of platinum oxide and hydrogenated at 50 psi. After 45 minutes, the theoretical amount of hydrogen was absorbed. The catalyst was removed by filtration in a nitrogen atmosphere through a bed of Celite and the bed washed several times with methanol. The filtrate and washes were immediately evaporated under reduced pressure. The yellow, gummy residue was dried at 50° C./0.1 mm for several hours to give crude product (IV).

EXAMPLE 3

7,8-Dimethyl-10-(1'-D-ribityl)-3H,10H-2,4-dioxopyrido[3,2-g]pteridine, (9-azariboflavin) (VI).

The compound (IV), prepared by the process set forth in Example 2, was dissolved in 220 ml. of dry pyridine and 6.5 g. (33 mmoles) of 5,5-dichlorobarbituric acid was added. The solution was heated at 55° C. for 2 hours in a nitrogen atmosphere with magnetic stirring. The reaction mixture was cooled and the black solid was filtered and washed several times with pyridine. The filtrate and washings were evaporated (bath 40° C.) under reduced pressure. The dark residue was dissolved in 100 ml. of methanol and cooled in the refrigerator overnight. The brown solid was filtered, washed with cold methanol and ether and recrystallized from 50 ml. of water (filtered while hot) to give 2.2 g. of 9-azariboflavin, m.p. 255°–258° C. (dec.).

Calc. for $C_{16}H_{19}N_5O_6$: C, 50.93; N, 5.08; N, 18.56.
Found : C, 50,67; N, 5.23; N, 18.25.

Although this invention has been described in relation to specific embodiments, it will be apparent that obvious modifications may be made by one skilled in the art without departing from the intended scope thereof as defined by the appended claims.

What is claimed is:

1. The compound of the structural formula:

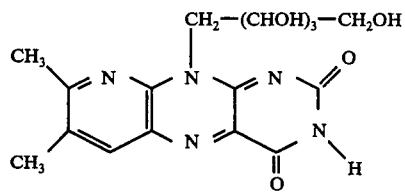

2. A pharmaceutically acceptable composition for the treatment of coccidiosis comprising an inert carrier and an effective amount of the compound of the structural formula:

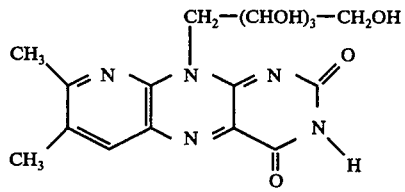

3. A composition according to claim 2 wherein said compound comprises from 0.0025 to 0.25% by weight of said composition.

4. A composition according to claim 3 wherein said compound comprises from 0.0125 to 0.05% by weight of said composition.

5. A composition according to claim 2 wherein said composition is a feed premix and said compound comprises from 0.1 to 50% by weight of the premix.

6. A composition according to claim 5 wherein said compound comprises from 0.5 to 25% by weight of said premix.

* * * * *